(12) United States Patent
Mirzaei et al.

(10) Patent No.: US 9,101,508 B2
(45) Date of Patent: Aug. 11, 2015

(54) ELECTRO SPUN NANOFIBROUS WOUND DRESSING AND A METHOD OF SYNTHESIZING THE SAME

(76) Inventors: Esmaeil Mirzaei, Tehran (IR); Reza Faridi Majidi, Tehran (IR); Saeed Sarkar, Tehran (IR); Seyed Mehdi Rezayat, Tehran (IR)

(*) Notice: Subject to any disclaimer, the term of this patent is extended or adjusted under 35 U.S.C. 154(b) by 899 days.

(21) Appl. No.: 13/313,033

(22) Filed: Dec. 7, 2011

(65) Prior Publication Data

US 2013/0150763 A1   Jun. 13, 2013

(51) Int. Cl.
| | |
|---|---|
| *A61F 13/00* | (2006.01) |
| *A61F 15/00* | (2006.01) |
| *B32B 5/00* | (2006.01) |
| *B32B 7/00* | (2006.01) |
| *B32B 5/12* | (2006.01) |
| *B32B 3/10* | (2006.01) |
| *D06N 7/04* | (2006.01) |
| *A61L 15/00* | (2006.01) |
| *A61F 13/02* | (2006.01) |
| *A61K 9/70* | (2006.01) |
| *A61K 9/00* | (2006.01) |
| *A61L 15/22* | (2006.01) |
| *A61L 15/44* | (2006.01) |
| *D04H 1/728* | (2012.01) |

(52) U.S. Cl.
CPC ........... *A61F 13/00029* (2013.01); *A61F 13/00* (2013.01); *A61F 13/00063* (2013.01); *A61F 13/02* (2013.01); *A61F 13/0203* (2013.01); *A61F 13/0206* (2013.01); *A61K 9/00* (2013.01); *A61K 9/70* (2013.01); *A61K 9/7007* (2013.01); *A61L 15/225* (2013.01); *A61L 15/44* (2013.01); *D04H 1/728* (2013.01); *A61L 2300/30* (2013.01); *A61L 2400/12* (2013.01)

(58) Field of Classification Search
CPC ................ A61F 13/00; A61F 13/0089; A61F 13/00314; A61F 13/00319; A61F 13/02; A61F 13/0203; A61F 13/0206; A61K 9/00; A61K 9/70; A61K 9/7007
USPC .............. 602/41–59; 424/443, 445, 447–449; 428/98, 105, 113, 137, 147, 172
See application file for complete search history.

(56) References Cited

U.S. PATENT DOCUMENTS 6,465,709 B1 * 10/2002 Sun et al. ................... 602/48
7,217,853 B2 *  5/2007 Kulichikhin et al. ........... 602/41

* cited by examiner

*Primary Examiner* — Victoria J Hicks
*Assistant Examiner* — Brandon L Jackson
(74) *Attorney, Agent, or Firm* — Barry Choobin; Patent 360

(57) ABSTRACT

The various embodiments herein provide an electro spun wound dressing comprising three nano fibrous layers and a method of synthesizing the same. The outer polymeric layer acts as a support layer for the other two layers and is hydrophilic in nature. The middle layer comprises a genipin cross linked reservoir layer loaded with a herbal extract of *Melilotus officinalis* and is hydrophobic or hydrophilic in nature. The second layer is cross-linked to control a release of the *Melilotus officinalis* extract in an aqueous environment. The third layer is a wound contacting inner layer comprising a non-cross-linked chitosan based nanofibrous layer that is hydrophilic in nature. Various additives are provided to enhance the mechanical or the chemical properties of the wound dressing and to control a release profile of the herbal extract.

19 Claims, 6 Drawing Sheets

ELECTRO SPUN NANOFIBROUS WOUND DRESSING AND A METHOD OF SYNTHESIZING THE SAME

BACKGROUND

1. Technical Field

The embodiments herein generally relate to the field of multi layered nanofibrous wound dressings and more particularly to an electro spun multi layered nanofibrous and polymeric wound dressing loaded with an herbal extract. The embodiments herein also relate to a method of synthesizing the electro spun polymeric wound dressing.

2. Description of the Related Art

The *Melilotus officinalis* extract is a major ingredient of a modified herbal based compound Semelil (ANGIPARS™), which is a promising candidate drug for wound healing. The results of the recent clinical trials showed that the new herbal extract, ANGIPARS™, is very effective for treatment of foot ulcers and authors suggest that this novel drug can be superior to other treatments and can be used in all types of ulcers. Experimental studies have shown no chronic or acute toxicity for ANGIPARS™.

The commercial product, ANGIPARS™, provides *Melilotus officinalis* extract in an oral form (capsule) and a topical form (3% cream) for the treatment of wounds. The major disadvantages with the oral and the topical forms are their administration for two or three times a day, need for exchanging a wound bandage after each administration and no/lack of dose control in each administration. This limits the application of *Melilotus officinalis* extract as a cream i.e. topical form for treatment of wounds.

On the other hand, the electro spun nanofibers have many characteristics that make them ideal candidates for wound healing applications. The electro spun nanofibers meet many characteristics of an ideal wound dressing. These include: efficiency as bacterial barrier, absorption of excess exudates or wound fluid, provision and maintenance of a moist environment or appropriate water vapor transmission rate, provision of adequate gaseous exchange, ability to conform to the contour of the wound area, functional adhesion, i.e., adherence to healthy tissue but non-adherence to wound tissue and painless to patient and ease of removal. The high surface area to volume ratio of the electro spun nanofibers facilitates oxygen permeability and allows fluid accumulation, which are highly desirable in the wound healing course. The pores in non-woven form of electro spun scaffolds (normally 1-10 μm) are small enough to prevent a bacterial penetration. Meanwhile the nanoscale fibers that impart the dressing with small interstices and high effective surface area can promote homeostasis. Such a function of homeostasis is activated from the physical feature of the nanofibrous dressings without using a haemostatic agent.

Further a therapeutic agent can be incorporated into the electro spun nanofibers to give them additional benefits for wound dressing applications. Antibiotics, growth factors and anesthetic are some therapeutic agents incorporated in the electro spun nanofibers used as wound dressing. Meanwhile a controlled release of therapeutics from the electro spun nanofibers is another benefit of the electro spun nanofibers as wound dressing.

WIPO patent application no. 2010/103324 A2 discloses an electro spun wound dressing comprising a biodegradable polymer or co-polymer and a nonsteroidal anti-inflammatory drug.

WIPO patent application no. 2008/010199 A2 discloses a mesh comprising nanofibers of oxidized polysaccharide and a fiber forming polymer.

WIPO patent application no. 2011/008842 A2 explains a preparation of electro spun silk fibroin/polyethylene oxide blend nanofibers as potential material for biomedical application such as wound dressing. The electro spun silk fibroin/PEO mates demonstrated suitable physical and bio-functional properties.

US patent application no. 2007/0155273 A1 discloses an electro spun biodegradable poly (ester-amid) fabric for biomedical application such as scaffold for tissue engineering and wound healing treatment. It also disclosed an incorporation of drug or other agent in poly (ester-amid) nanofibers to accelerate a healing.

Considering the benefits of the electro spun nanofibers as wound dressing and limitations of *Melilotus officinalis* extract cream, the incorporation of *Melilotus officinalis* extract within the electro spun nanofibers can lead to a development of an efficient device for wound healing application.

On the other hand, a wide range of natural and synthetic polymers can be electro spun into nanofibers matrices with structural integrity and specific fiber arrangements. Polymers used in electro spun membranes as wound dressing include collagen, gelatin, fibrinogen, chitosan, PU, PCL, PLA, and PLGA, or some blends of them.

Chitosan (CS), a biopolymer comprising glucosamine and N-acetyl glucosamine, is an N-deacetylated product of chitin and one of the most abundant polysaccharides in nature. Chitosan has many advantages such as biocompatibility, biodegradability, haemostatic activity, anti-infection and wound healing acceleration properties when used in a wound dressing application For these reasons, chitosan has been one of the important biomaterials for a wound management in the recent years. An electro spinning of chitosan to a fibrous structure is difficult because it has a poly cationic character in an acidic aqueous solution due to the many amino groups in its backbone. Its poly cationic nature excessively increases the surface tension of the solution. Nevertheless, the fibrous structures were successfully formed by the electro spinning chitosan solutions in 90 wt % aqueous acetic acid solutions or by using an environmentally harmful and toxic solvent like trifluoro acetic acid (TFA) or TFA/dichloromethane (DCM). Since the electro spinning of chitosan itself proved to be difficult, chitosan was mixed with other synthetic or natural polymers, such as PEO, PVA, poly(lactic acid) (PLA) or its copolymers, silk fibroin (SF), and collagen. The resultant chitosan fibers need to be cross-linked to maintain their structural integrity, as they can readily swell in an aqueous solution. Glutaraldehyde (GA) is commonly used for cross-linking chitosan nanofibers. However GA is a toxic reagent and hence is not proper/advised for use in biological systems.

A water-soluble bi-functional natural cross linking reagent, genipin, has been used for cross linking the chitosan in the form of a film or particles. The resulting cross-linked complexes are not cytotoxic for the animal and human cells examined so far. The safety and the beneficial actions of the genipin emerge from a number of research projects for the therapies in the areas of diabetes, periodontitis, cataract, hepatic dysfunction, as well as in wound repair and nerve regeneration. But none of the prior arts provides an electro spun nanofibers incorporated with an herbal extract and cross-linked using genipin.

The *Melilotus officinalis* extract in a topical form is not provided. The *Melilotus officinalis* extract in a topical form obviates cream limitation and also provides additional benefits for wound healing purposes. Also, a cross-linking of chitosan nanofibers with a low toxic reagent is required.

Hence there is a need to provide a wound dressing containing an herbal extract with cross linked nanofibers to provide a controlled release of the herbal extract in a wound.

The above mentioned shortcomings, disadvantages and problems are addressed herein and which will be understood by reading and studying the following specification.

OBJECTIVES OF THE EMBODIMENTS

The primary object of the embodiments herein is to provide an electro spun nanofibrous wound dressing containing an herbal medicament.

Another object of the embodiments herein is to provide a *Melilotus officinalis* extract wound dressing based on the electro spun nanofibers.

Yet another object of the embodiments herein is to provide an electro spun nanofibrous wound dressing to release the medicament in a controlled manner.

Yet another object of the embodiments herein is to provide an adhesive wound dressing that is adhered to a wound surface and removed from the wound easily without any wound damage or pain.

Yet another object of the embodiments herein is to provide a *Melilotus officinalis* extract in a topical form to obviate a cream limitation and also to give additional benefits for wound healing purposes.

Yet another object of the embodiments herein is to provide a method of synthesizing an electro spun wound dressing comprising a herbal extract.

These and other objects and advantages of the embodiments herein will become readily apparent from the following detailed description taken in conjunction with the accompanying drawings.

SUMMARY

The various embodiments herein provide an electro spun polymer based wound dressing loaded with *Melilotus officinalis* extract. The wound dressing comprises a multi-layer or a single-layer of electro spun nanofibers.

According to one embodiment herein, an electro spun nanofibrous wound dressing comprises a first nanofibrous layer, a second nano fibrous layer and a third nano fibrous layer. The first nanofibrous layer is a polymeric layer. The first nanofibrous layer is an outer supporting layer. The first nanofibrous layer is hydrophobic in nature.

The second nanofibrous layer is a polymeric layer. The second nanofibrous layer is a genipin cross linked middle reservoir layer loaded with an herbal extract. The second nanofibrous layer is hydrophobic or hydrophilic in nature. The herbal extract is *Melilotus officinalis* extract. The cross-linking of the second nanofibrous layer controls a release of the *Melilotus officinalis* extract in an aqueous environment.

The third nanofibrous layer is a polymeric layer. The third nanofibrous layer is a wound contacting inner layer. The third nanofibrous layer is a non-cross-linked chitosan based nanofibrous layer. The third nanofibrous layer is hydrophilic in nature.

According to the embodiments herein, the wound dressing comprises various additives. The additives are selected from a group consisting of surfactants, block-co-polymers, salts and rubbers. The additives help to enhance the mechanical or chemical properties of the wound dressing and control a release profile of the herbal extract.

The first nanofibrous layer comprises biocompatible polymers. The biocompatible polymers are hydrophobic polymers. The hydrophobic polymers are selected from a group consisting of polyamides, polycaprolactone (PCL), poly (lactic acid) (PLA), poly (lactic-co-glycolic acid) (PLGA) and a combination thereof. The first nanofibrous layer controls a vapour transmission rate and provides a moist environment on a surface of a wound in order to accelerate a wound healing process and also provides a barrier against a bacteria penetration thereby preventing the wound from an infection.

The second nanofibrous layer comprises hydrophilic polymers or hydrophobic polymers or a combination thereof and an extract of *Melilotus officinalis*. The hydrophobic polymers are selected from a group consisting of polyamides, polycaprolactone (PCL), poly (lactic acid) (PLA), poly(lactic-co-glycolic acid) (PLGA), and a combination thereof, and wherein the hydrophilic polymers are selected from a group consisting of chitosan, gelatin, collagen, poly vinyl alcohol (PVA), polyethylene oxide (PEO), and a combination thereof, and wherein the hydrophilic polymer is chitosan. The second nanofibrous layer comprises chitosan and poly ethylene oxide (PEO) preferably. The extract of *Melilotus officinalis* is mixed to the second nanofibrous layer at a ratio of 50%, or 30% or 10% of a total weight of the second nanofibrous layer. The chitosan is present in the second nanofibrous layer at a ratio of up to 90 weight percent of second nanofibrous layer or less. The genipin is present in the second nanofibrous layer at a ratio of 0.5-10% of chitosan by weight. The cross-linking of the chitosan based nanofibers with genipin decreases an initial burst release of an herbal extract and prolongs a release rate of the herbal extract. The second nanofibrous layer has a high water absorption capability and absorbs the excess exudates coming out from a wound and treats wounds with high exudates. The second nanofibrous layer is structurally stable in water.

The third nanofibrous layer comprises biocompatible hydrophilic polymers. The biocompatible hydrophilic polymers are selected from a group consisting of chitosan, collagen, gelatin, poly vinyl alcohol (PVA), polyethylene oxide (PEO) and a combination thereof. The third nanofibrous layer comprises chitosan and poly ethylene oxide (PEO). The chitosan is present in the third nanofibrous layer at a ratio of 90 weight percent of polymer or less. The third nanofibrous layer forms a gel in a presence of water and the gel forming ability of the third nanofibrous layer helps the wound dressing to be removed from a wound easily in the presence of water. The third nanofibrous layer forms a barrier that controls a release of *Melilotus officinalis* extract from the second nanofibrous layer.

According to an embodiment herein, the release rate of the herbal extract depends on a type of polymer used, an amount of the herbal extract loaded, an extent of cross linking of the polymer and an addition of another polymer and additives.

According to another embodiment herein, a method of synthesizing an electro spun nanofibrous wound dressing comprises steps of forming a first nanofibrous layer, forming a second nanofibrous layer on the formed first nanofibrous layer, forming a third nanofibrous layer on the formed second nanofibrous layer, and exposing the formed first nanofibrous layer, the second nanofibrous layer and the third nanofibrous layer to a water vapour at 30° C. for 24 h to obtain the final wound dressing.

The first nanofibrous layer is a polymeric layer. The first nanofibrous layer is in a form of a mat. The first nanofibrous layer acts as a support layer for a second nanofibrous layer and a third nanofibrous layer.

The second nanofibrous layer is a polymeric layer. The second nanofibrous layer is a chitosan polymer based nanofibrous layer loaded with *Melilotus officinalis* extract.

The third nanofibrous layer is a polymeric layer. The third nanofibrous layer is a chitosan polymer based layer without *Melilotus officinalis* extract.

According to an embodiment herein, the electro spun nanofibrous wound dressing is synthesized by an electro spinning process. The electro spinning process is carried out using an electro spinning device. The electro spinning device has a voltage in a range of 1-35 kV and a syringe pump. The syringe pump is controlled to provide a flow rate in a range of 0.1-100 ml/h. The electro spinning is carried out at a temperature of 30° C. The electro spinning is carried at a speed of 15 rpm.

According to another embodiment herein, the step of forming the first nanofibrous layer further comprises electro spinning a solution of polyamide 6, 6. The solution of polyamide 6, 6 is a 20% (w/v) solution in a solvent. The solvent comprises a solution of formic acid and water in a ratio of 90/10 v/v. The device for electro spinning is kept at a voltage of 15 kV. The nozzle to a collector distance of an electro spinning device is kept at 10 cm. The injection rate of the solution of polyamide 6, 6 is fixed at 1 ml/h for the process.

The step of forming the second nanofibrous layer further comprises a preparation of chitosan solution in 80% (v/v) aqueous acetic acid solution. The chitosan solution is a 3% by weight solution. Further, a poly ethylene oxide (PEO) solution in 80% (v/v) aqueous acetic acid solution is prepared. The PEO solution is a 3% by weight solution. The prepared chitosan solution and the prepared poly ethylene oxide (PEO) solution are mixed to form a blend solution of Chitosan and PEO in different weight ratios. The different weight ratios are 90/10 to 50/50. A *Melilotus officinalis* extract solution in 80% (v/v) aqueous acetic acid is prepared. The *Melilotus officinalis* extract solution has a concentration of 20% (w/w) concentration. The prepared *Melilotus officinalis* extract solution is mixed with the blend solution of Chitosan and PEO to obtain a polymeric extract solution. The polymer to extract weight ratios of 100/0 to 50/50. A 10% genipin solution in ethanol is prepared. The prepared genipin solution is added to the obtained polymeric extract solution. The genipin solution is added at an amount of 0.5 to 10 wt % of the chitosan in the polymeric extract solution. The polymeric extract solution including the genipin is electro spun on the formed first nanofibrous layer. The electro spinning is done at a voltage of 20 kV. The distance between a nozzle to a collector of an electro spinning device is kept at 12 cm and an injection rate of the polymeric extract solution including the genipin is kept at 1 ml/h, according to one embodiment herein.

The step of forming the third nanofibrous layer further comprises a preparation of chitosan solution in 80% (v/v) aqueous acetic acid. The chitosan solution is a 3% by weight solution. Then, a poly ethylene oxide (PEO) solution in 80% (v/v) aqueous acetic acid solution is prepared. The PEO solution is a 3% by weight solution. The prepared chitosan solution and prepared poly ethylene oxide (PEO) solution are mixed to form a blend solution of Chitosan and PEO in different weight ratios. The different weight ratios are 90/10 to 50/50. The blend solution of Chitosan and PEO is electro spun on the formed second nanofibrous layer. The electro spinning is done at a voltage of 20 kV. The distance between a nozzle to a collector of an electro spinning device is kept at 12 cm and wherein an injection rate of the blend solution of Chitosan and PEO is kept at 1 ml/h, according to one embodiment herein.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a polymer based nanofibrous wound dressing incorporated with *Melilotus officinalis* extract synthesized using electro spinning process.

According to the embodiments herein, the wound dressing has three nanofibrous layers. The three layers are a hydrophobic nanofibrous layer named outer layer or support layer, a genipin cross-linked chitosan based nanofibrous layer incorporated with *Melilotus officinalis* extract named middle layer or reservoir layer and a wound contacting non-cross-linked chitosan based nanofibrous layer named inner layer or wound contacting layer. The layers are fibrous in nature. The outer layer which acts as a support layer. The middle layer acts as a reservoir for *Melilotus officinalis* extract, and the wound contacting inner layer helps in controlling the release of the *Melilotus officinalis* extract. The layers are polymeric in nature. The outer layer is named hydrophobic nanofibrous layer. The middle layer is a nanofibrous layer or reservoir layer comprising *Melilotus officinalis* extract, and the inner layer is wound contacting hydrophilic layer.

According to one embodiment herein, the outer layer comprises hydrophobic polymers such as polyamides or polycaprolactone (PCL) or poly (lactic acid) (PLA) or poly (lactic-co-glycolic acid) (PLGA) or blend of them.

According to an embodiment herein, the middle layer comprises hydrophobic or hydrophilic polymers or blend of them and a *Melilotus officinalis* extract. The hydrophobic polymers are polyamides or polycaprolactone (PCL) or poly (lactic acid) (PLA) or poly (lactic-co-glycolic acid) (PLGA) or blend of them. The hydrophilic polymers are chitosan or gelatin or collagen or poly vinyl alcohol (PVA) or polyethylene oxide (PEO) or blend of them. The chitosan constitutes 90 weight percentage of polymer or less. The *Melilotus officinalis* extract constitute 50% of total weight of middle layer or less. The *Melilotus officinalis* extract gets released in an aqueous environment. The release of *Melilotus officinalis* extract in aqueous environment is controlled by the cross-linking of the polymers or an addition of polymers or other additives. The polymers in the middle layer preferably comprise chitosan and poly ethylene oxide (PEO). The chitosan in the middle layer is cross-linked by genipin. The genipin is 0.5-10% of chitosan by weight. The middle genipin-cross-linked layer is structurally stable in water. The non-cross-linked wound contacting inner layer forms a gel in an aqueous environment.

According to an embodiment herein, the inner layer comprises hydrophilic polymers such as chitosan or gelatin or collagen or poly vinyl alcohol (PVA) or polyethylene oxide (PEO) or blend of them. The inner layer comprises chitosan and poly ethylene oxide (PEO). The chitosan constitute 90 weight percent of polymer or less.

According to a preferred embodiment herein, the wound dressing constitute of three nanofibrous layers. The three nanofibrous layers are: a hydrophobic outer layer as supporting layer, a hydrophobic or hydrophilic middle layer as *Melilotus officinalis* extracts reservoir and a hydrophilic inner layer as wound contacting layer. The hydrophobic outer layer is from biocompatible polymers. The hydrophobic polymers can be PCL, PLA, PLGA, polyamides or other hydrophobic polymers or blend of them. According to the embodiments herein, the hydrophobic outer layer is a support for inner layers. The hydrophobic outer layer controls a vapor transmission rate and provides a moist environment on the surface of the wound in order to accelerate a wound healing process.

The hydrophobic outer layer also provides a barrier against a bacteria penetration which prevents a wound from an infection.

According to one embodiment herein, *Melilotus officinalis* extract has been loaded in the middle fibrous layer. *Melilotus officinalis* extract can be embedded in the middle layer by mixing a polymer and an extract solution and then electro spinning of the mixed solution, or it can be physically absorbed on the surface of the nanofibers after an electro spinning process and a fiber production. Therefore the middle layer is a reservoir for *Melilotus officinalis* extract. In a preferred embodiment, *Melilotus officinalis* extract is present in a ratio of 50%, 30% or 10% of total weight of the middle layer.

Preferably, the polymers of the middle layer are of biocompatible hydrophilic or hydrophobic polymers or a blend of them. Some of the biocompatible polymers for the middle layer can be chitosan, PCL, PLA, PLGA, gelatin, collagen, silk fibroin, PEO, PVA and polyurethane or a blend of them.

According to one embodiment, the middle layer can be hydrophilic polymers with a high water absorption capability. This gives the middle layer with an additional benefit of absorbing the excess exudates from a wound which is desirable for a treatment of the wounds with high exudates.

According to an embodiment, the middle layer can be from hydrophobic polymers. This gives the middle layer with an additional benefit of maintaining a moist environment on the surface of the wound which is desirable for a treatment of wound with no exudates.

Preferably, a wound contacting inner layer comprises biocompatible hydrophilic polymers such as chitosan, collagen, gelatin, PVA, and PEO or a blend of them. In a preferred embodiment, the wound contacting inner layer forms a gel in a presence of water. This gel forming layer enables the dressing to be removed from a wound easily in the presence of water. The inner layer can also be a barrier to control a release of *Melilotus officinalis* extract from the middle layer.

The electro spun nanofibrous membranes have some attributes that make them a good candidate for a wound healing application. The benefits of an electro spun nanofibrous mat for a wound dressing application are as follows: absorbability, semi-permeability, homeostasis and structure similar to an extra cellular matrix.

On the other hand, chitosan is a non-toxic biocompatible and biodegradable biopolymer that has an antibacterial activity. Chitosan also accelerates a wound healing process and reduces a wound healing period. Therefore, the chitosan is a proper material for use in wound dressing objects.

In addition to the above, *Melilotus officinalis* extract, a compound that is used for healing chronic wounds have shown good therapeutic effects and has no acute or chronic toxicity. Therefore, an incorporation of *Melilotus officinalis* extract in the electro spun nanofibrous mats provides an efficient wound dressing. The *Melilotus officinalis* extract based wound dressing with electro spun nanofibers releases the *Melilotus officinalis* extract from the electrospun nanofibers in a controlled manner. The controlled release of the *Melilotus officinalis* extract is based on the different types of polymers or co-polymers or other additive agents used and added to the nanofibers, or the cross linking of the nanofibers. The *Melilotus officinalis* extract loaded middle layer has been cross-linked to reduce a release rate of the extract.

According to the embodiments herein, the mesh formed by the cross linking of polymers is used in a wound dressing and the dressing has multiple layers. The wound dressing disclosed in the embodiments herein is an adhesive wound dressing that adheres to a wound surface and gets easily removed from the wound without any wound damage or pain. This is because of the hydrophilic nature of the inner layer. The wound contacting inner layer selected from hydrophilic polymers is easily removed from a wound in the presence of water.

According to one embodiment herein, the three layers of wound dressing are synthesized by an electro spinning of the three different polymers or polymer/extract solutions sequentially. The three different polymers or polymer/extract solutions are first prepared and then electro spun respectively to produce the three-layered wound dressing. The steps are as follows:

Producing Wound Dressing Outer Layer:

A proper polymer solution (for example 20% (w/v) polyamide solution in formic acid/water (90/10 v/v)) is first prepared and then electro spun at an optimized electro spinning condition (i.e. applied voltage, nozzle to collector distance, injection rate and temperature) to obtain a polymer nanofibrous mat on an electro spinning collector. This nanofibrous mat on the collector is considered as a wound dressing support layer (first layer) which is used as a support layer for the middle layer and the inner layers. The other two layers (middle and inner layer) are then formed on the first layer.

The outer layer of the wound dressing is formed from different hydrophobic polymers i.e. polyamides, PAN, PCL, PLA, and PLGA or other hydrophobic polymers or a blend of them. The type of solvent, polymer(s) concentration, and electro spinning condition are different for each polymer to produce a nanofibrous mat.

Producing Wound Dressing Middle Layer:

The nanofibrous middle layer (second layer) which is loaded with *Melilotus officinalis* extract is formed on the previously formed support layer by the electro spinning of a polymer/extract solution. A proper polymer solution (e.g. 3 wt % Chitosan/PEO (90/10) in 80% (v/v) aqueous acetic acid solution) and *Melilotus officinalis* extract solution (20% (w/w) in 80% (v/v) aqueous acetic acid solution) is first prepared. The polymer solution and *Melilotus officinalis* extract solution are then mixed to obtain a polymer/extract solution with different polymers to extract a weight ratio (e.g. 100/0 to 50/50). The polymer/extract solution is electro spun on the previously formed support layer to form a nanofibrous mat incorporated with *Melilotus officinalis* extract which is considered as the middle layer of wound dressing. This middle layer is a reservoir for *Melilotus officinalis* extract and releases it when the dressing is exposed to an aqueous media.

The polymers for the middle layer are made from different hydrophilic or hydrophobic polymers or a blend of them. Some polymers for the middle layer can be chitosan, PCL, PLA, PLGA, gelatin, collagen, silk fibroin, PEO, PVA and polyurethane or a blend of them. The solution properties and an electro spinning condition for each polymer for mixing them with *Melilotus officinalis* extract and for forming a nanofibrous mat loaded with the extract are different.

Producing Wound Dressing Inner Layer:

The nanofibrous inner layer (third layer) is formed on the previously formed middle layer. A proper polymer solution (for example 3 wt % Chitosan/PEO (90/10) in 80% (v/v) aqueous acetic acid solution) is first prepared and then electro spun is carried out on the previously formed middle layer to form a nanofibrous mat. This nanofibrous mat is considered as an inner layer or a wound contacting layer. The inner layer is formed from different hydrophilic polymers such as chitosan, collagen, gelatin, PVA, and PEO or blend of them. To form an electro spun nanofibrous mat, various solution properties and an electro spinning condition is required for each polymer.

The solution properties (including, concentration, viscosity, surface tension, conductivity and pH) and the electro spinning condition (including, applied voltage, tip to collector distance, injection rate and temperature) are different for various polymers of each layer. The electro spinning is carried out at 30° C.

The middle layer can be formed from hydrophilic or hydrophobic polymers or blend of them. Since the middle layer is loaded with *Melilotus officinalis* extract, the release profile of the extract depends on some parameters like the kind of polymer in the middle layer. The type of the polymer in the middle layer also affects a water absorption capacity of the middle layer. The hydrophilic polymers have a high water absorption capability and so give the middle layer with an additional benefit of absorbing the excess exudates from a wound which is desirable for a treatment of the wounds with high exudates. The middle layer also can be formed from hydrophobic polymers. This gives the middle layer with an additional benefit of maintaining a moist environment on the surface of the wound which is desirable for a treatment of the wound with no exudates. Choosing more preferable polymer for the middle layer depends on the type of the wound and also an expected release profile of the extract. Therefore the middle layer can be formed from hydrophilic polymers or hydrophobic polymers or a blend of then.

Several additives can be added to the wound dressing in order to enhance the mechanical or chemical properties of a wound dressing and to control the release profile of the extract. These additives can be selected from a group comprising various surfactants, block co polymers, salts, rubbers, and so on.

The *Melilotus officinalis* extract is incorporated in the nanofibrous polymeric matrix of a wound dressing. If the polymeric matrix of the wound dressing has functional groups such as —$NH_2$, the release profile of the extract can be controlled by cross linking the polymeric matrix with the a special cross-linking agent such as glutaraldehyde or genipin. Furthermore, addition of other polymers or surfactants such as block-co-polymers in polymeric matrix of wound dressing which loaded with extract can be used to control a release behavior of the extract from wound dressing.

Figure 1:
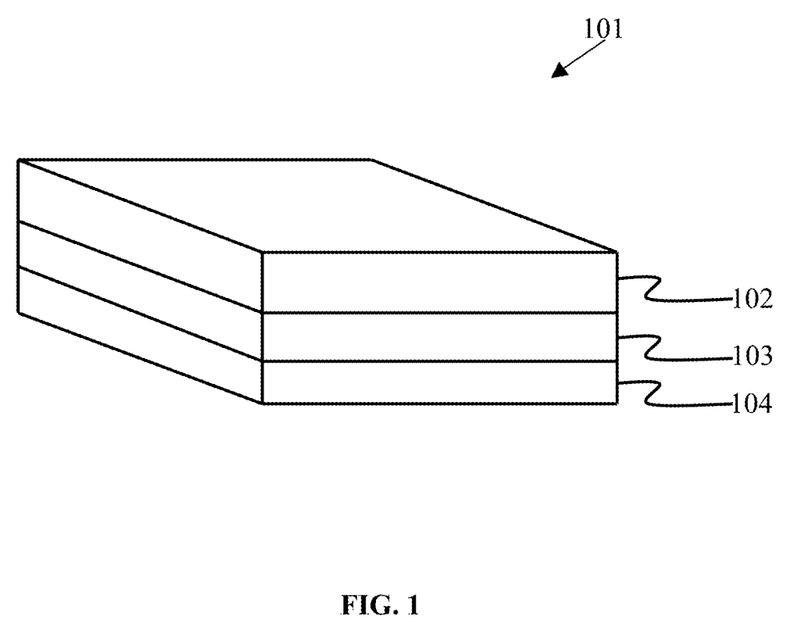
FIG. 1 shows a schematic diagram of the three-layered electro-spun nanofibrous wound dressing, according to an embodiment herein.

FIG. 1 shows a schematic diagram of the three-layered electro spun nanofibrous wound dressing, according to an embodiment herein. With respect to FIG. 1, the multi layered wound dressing 101 comprises an outer support layer 102, a middle reservoir layer 103 and a wound contacting inner layer 104.

Figure 2:
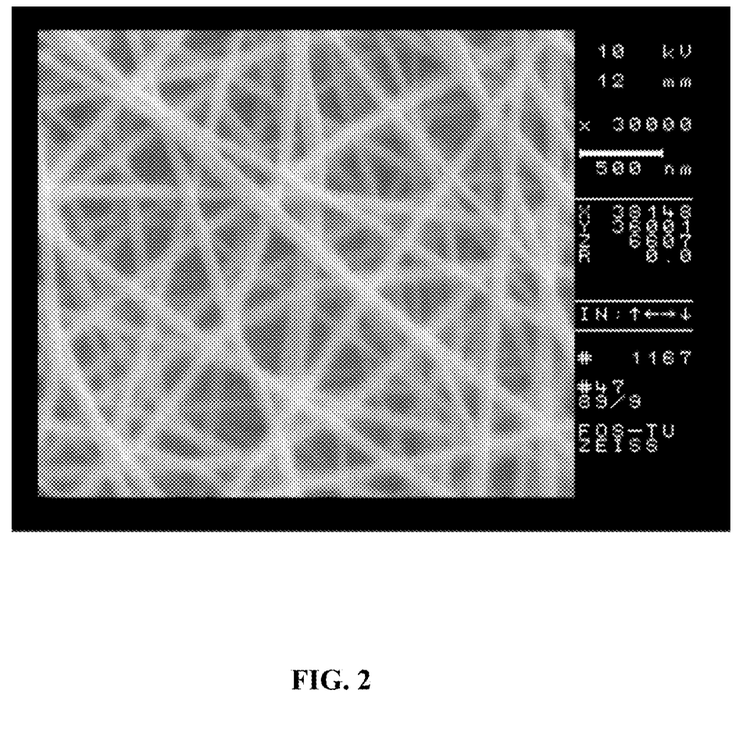
FIG. 2 shows a scanning electron microscopic (SEM) image of polyamide outer layer in a three-layered electro-spun nanofibrous wound dressing, according to an embodiment herein.

FIG. 2 shows a scanning electron microscopic (SEM) image of polyamide outer layer, in a three-layered electro spun nanofibrous wound dressing according to an embodiment herein. With respect to FIG. 2, the nanofibrous structure of the outer layer is demonstrated. The scale bar for the FIG. 2 is 500 nm. The layer was prepared by electro spinning of 20% (w/v) polyamide 6, 6 solutions in formic acid/water (90/10 v/v). According to the preferred embodiment, the outer layer is an electro spun nanofibrous mat obtained from an electro spinning of polyamide 6, 6 in a formic acid/water (90/10 v/v) solution. The outer layer acts as a support for the middle layer and the inner layers. The polyamide outer layer also prevents bacteria from penetrating into a wound and maintains and provides a moist environment on the surface of the wound.

The electro spun chitosan based nanofibrous layer loaded with *Melilotus officinalis* extract had been synthesized on the polyamide outer layer. This layer acts as a middle layer. Since chitosan alone was not electro spinnable in an aqueous solution, PEO was added to chitosan solution as copolymer to make the chitosan electro spinnable. The proportion of chitosan in the polymer solution (chitosan/PEO) was up to 90% by total weight of the polymer in the solution. *Melilotus officinalis* extract was then added to the polymer solution and electro spun was carried out to make chitosan based nanofibrous middle layer loaded with *Melilotus officinalis* extract. *Melilotus officinalis* extract proportion was 0-50% by weight of the electro spun chitosan based nanofibrous middle layer.

Figure 3A:
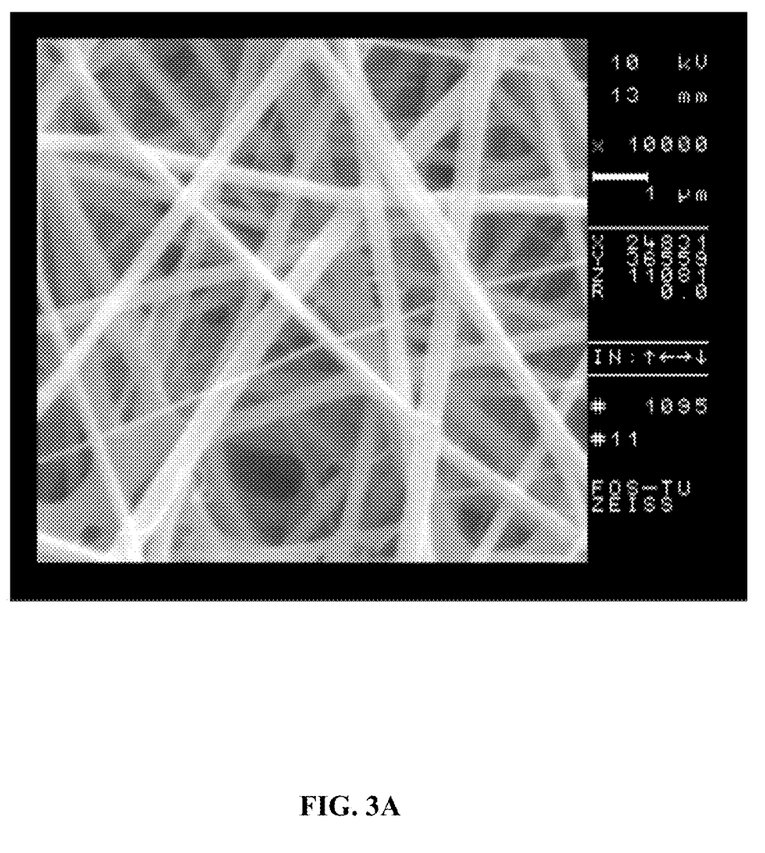
FIG. 3A shows a scanning electron microscopic (SEM) image of non-cross-linked chitosan based nanofibrous (CS/PEO 90/10) middle layer loaded with 30 wt % *Melilotus officinalis* extract before immersion in phosphate buffer solution (PBS) (Ph=7.4) at 37° C. for 48 h, in a three-layered electro-spun nanofibrous wound dressing according to an embodiment herein.
Figure 3B:
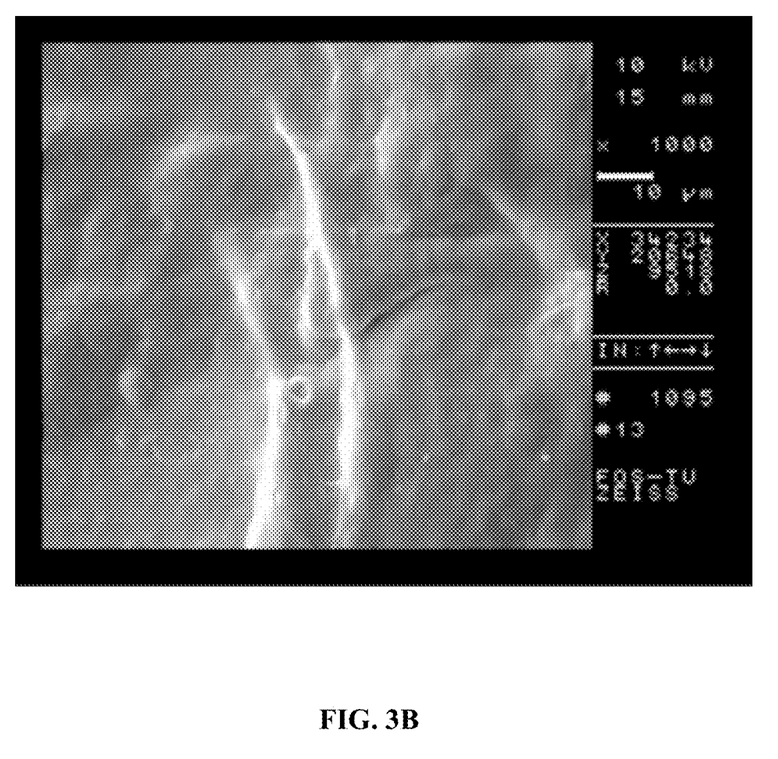
FIG. 3B shows a scanning electron microscopic (SEM) image of non-cross-linked chitosan based nanofibrous middle layer loaded with 30 wt % *Melilotus officinalis* extract after immersion in PBS (Ph=7.4) at 37° C. for 48 h, in a three-layered electro-spun nanofibrous wound dressing according to an embodiment herein.

FIG. 3A shows a scanning electron microscopic (SEM) image of non-cross-linked chitosan based nanofibrous (CS/PEO 90/10) middle layer loaded with 30 wt % *Melilotus officinalis* extract before immersion in phosphate buffer solution (PBS) (pH=7.4) at 37° C. for 48 h, in a three-layered electro spun nanofibrous wound dressing according to an embodiment herein. FIG. 3B shows a scanning electron microscopic (SEM) image of non-cross-linked chitosan based nanofibrous middle layer loaded with 30 wt % *Melilotus officinalis* extract after immersion in PBS (pH=7.4) at 37° C. for 48 h, in a three-layered electro spun nanofibrous wound dressing according to an embodiment herein. With respect to FIG. 3A and FIG. 3B, the non-cross-linked chitosan based middle layer is not stable in an aqueous environment and lost its fibrous structure after 48 h of immersion in PBS. The scale bar for FIG. 3A and FIG. 3B is 1 μm and 10 μm respectively.

Figure 4:
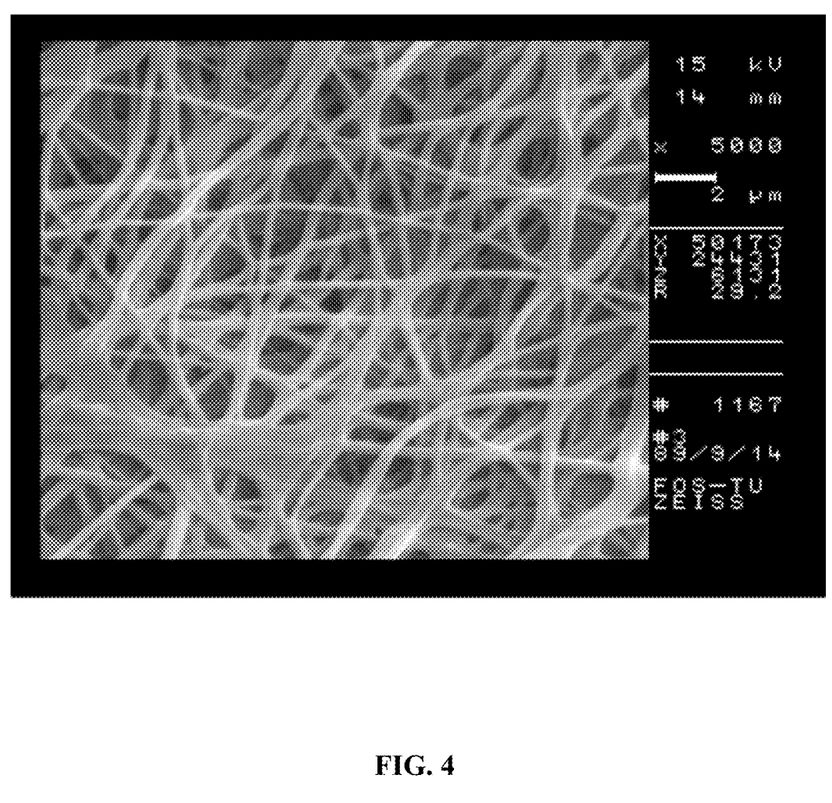
FIG. 4 shows a scanning electron microscopic (SEM) image of genipin cross-linked chitosan based nanofibrous (CS/PEO 90/10) middle layer loaded with 30 wt % *Melilotus officinalis* extract after immersion in PBS (pH=7.4) at 37° C. for 48 h, in a three-layered electro-spun nanofibrous wound dressing according to an embodiment herein.

Glutaraldehyde is a common reagent that is used for cross-linking chitosan nanofibers. However, glutaraldehyde is toxic in nature and cannot be used in the biological systems. In the embodiments herein, genipin was used instead of glutaraldehyde for cross linking the chitosan polymeric layers. Genipin is a non-toxic biodegradable natural reagent. Genipin cross-linked chitosan based nanofibrous middle layer loaded with 30 wt % *Melilotus officinalis* extract was immersed in PBS (pH=7.4) at 37° C. for 48 h.

FIG. 4 shows an SEM image of genipin cross-linked chitosan based nanofibrous (CS/PEO 90/10) middle layer loaded with 30 wt % *Melilotus officinalis* extract after immersion in PBS (pH=7.4) at 37° C. for 48 h, in a three-layered electro spun nanofibrous wound dressing according to an embodiment herein. With respect to FIG. 4, the genipin cross-linked chitosan based nanofibers were stable in PBS (pH=7.4) and maintained their fibrous structure. The scale bar for FIG. 4 is 2 μm.

*Melilotus officinalis* extract is released from the chitosan based middle layer in an aqueous media. As a result of it, the *Melilotus officinalis* extract gets released from the wound dressing and delivered to the wound, when the wound dressing is placed on a wound surface.

Figure 5:
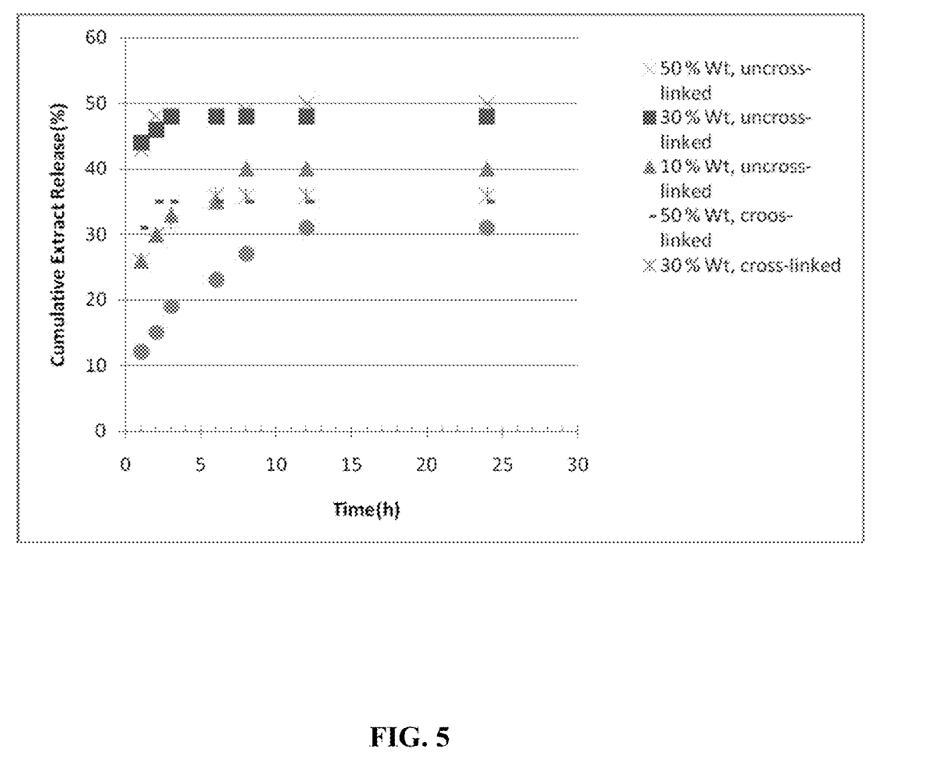
FIG. 5 shows a graphical representation of a release profile of *Melilotus officinalis* extract from the wound dressing in PBS (pH=7.4) at 37° C., according to an embodiment herein.

FIG. 5 shows a graphical representation of a release profile of *Melilotus officinalis* extract from the wound dressing in PBS (pH=7.4) at 37° C., according to an embodiment herein. With respect to FIG. 5, the symbols indicates the amount of layer (wt %) and cross-linking of nanofibers in the middle layer for each sample, and wherein the symbol 'X' indicates a sample in which an amount of *Melilotus officinalis* extract in the middle layer is 50 wt % and the chitosan based nanofibers in the middle layer is uncross-linked, and wherein the symbol '■' indicates a sample in which amount of *Melilotus officinalis* extract in middle layer is 30 wt % and the chitosan based nanofibers in middle layer is uncross-linked, and wherein the symbol '▲' indicates a sample in which an amount of *Melilotus officinalis* extract in middle layer is 10 wt % and the chitosan based nanofibers in middle layer is uncross-linked, and wherein the symbol '--' indicates a sample in which an amount of *Melilotus officinalis* extract in the middle layer is 50 wt % and the chitosan based nanofibers in the middle layer is cross-linked, and wherein '*' indicates a sample in which an amount of *Melilotus officinalis* extract in the middle layer is 30 wt % and the chitosan based nanofibers in middle layer is cross-linked, and wherein '●' indicates a sample in which an amount of *Melilotus officinalis* extract in the middle layer is 50 wt % and the chitosan based nanofibers in the middle layer is cross-linked. The effect of an amount of *Melilotus officinalis* extract in the middle layer (wt %) and the cross-linking of chitosan based nanofibers in the middle layer on the release behavior of the extract is shown. The release profiles of *Melilotus officinalis* extract from the chitosan based dressing depend on the loading capacity of the extract and the cross-linking of nanofibers in middle layer. According to FIG. 5, a burst release of a drug was observed for all the samples after 1 h incubation in the PBS. The samples with a lower amount of extract in the middle layer exhibit a gradual increase in the cumulative release of the extract after an initial burst release. Also, the cross-linking of the chitosan based nanofibers in the middle layer decreases the initial burst release of the extract and prolongs a release rate at longer times. The release rate of the medicament (extract) depends on various parameters like the type of polymer, an amount of loaded extract, the extent of cross linking of the polymer and an addition of other polymers or additives. The effect of the amount of loaded extract as well as cross-linking on a release profile is shown in FIG. 5. According to FIG. 5, the cross-linking of the chitosan based nanofibers with genipin decreases the initial burst release of the extract and prolongs a release rate at longer times.

EXPERIMENTAL DATA

Example 1

Materials

Nylon-6, 6 (Polyamide-6, 6) was of technical grade (medium viscous, DSM Co., The Netherlands). Formic acid (98-100%) was purchased from Merck chemicals co. (Germany). Chitosan (LMW, degree of deacetylation, 91.2%) was purchased from Eastar Group (Dong Chen) Co., Ltd., (china). Polyethylene oxide (PEO) (MW 900 KD) was purchased from Acros Organics Co. Glacial acetic acid was purchased from Merck Chemical. Genipin (GP), methyl-2-hydroxy-9-(hydroxymethyl)-3-oxabicyclonona-4,8-diene-5-carboxylate was obtained from Challenge Bioproducts Co. Ltd. (Touliu, Taiwan). *Melilotus officinalis* extract was obtained from Pars Roos Co. (Iran).

Example 2

Electro Spinning Process

The electro spinning process was carried out using Electroris® (FNM Ltd., Iran, www.fnm.ir) as an electro spinner device having a high voltage and a syringe pump controllable in a range of 1-35 kV and 0.1-100 ml/h, respectively. This device is able to control the electro spinning parameters such as an injection rate, a drum speed, a working distance (needle-collector distance), a needle scanning rate and a temperature of the electro spinning media. The polymer solutions were placed into a 5 mL plastic syringe with a metallic blunt-ended 18G needle as a nozzle for electro spinning. A sheet of aluminum foil was wrapped on the drum of an electro spinner device which was used as grounded collector. A syringe pump was fed solution to the needle tip and a positive high voltage was connected to a metallic needle and the collector was connected to ground and the speed of drum was fixed at 15 rpm. The electro spinning process was carried out at 30° C.

Example 3

Producing Nanofibrous Polyamide Outer Layer

Nylon-6, 6 (Polyamide-6, 6) was first dissolved in a formic acid/water (90/10 v/v) solution to prepare a 20% (w/v) polyamide solution. The polyamide solution was placed into a 5 mL plastic syringe and put into an electro spinner device. The applied voltage, a nozzle to collector distance and an injection rate were fixed at 15 kV, 10 cm and 1 ml/h, respectively. The polyamide nanofibers were formed on the aluminum collector which was used as a support layer for the middle layer and the inner layer.

Example 4

Producing Chitosan Based Middle Layer Loaded with *Melilotus officinalis* Extract 0.3 grams of chitosan powder and 0.3 grams of PEO powder were first dissolved in a 9.7 grams of 80% (v/v) aqueous acetic acid solution separately and stirred at 30° C. for 24 h to obtain 3 wt % chitosan and PEO solutions. The Chitosan solution and the PEO solution were mixed at different weight ratios and stirred at 30° C. for 1 h to obtain a Chitosan/PEO blend solution with a Chitosan to PEO weigh ratio in the range of 90/10 to 50/50. *Melilotus officinalis* extract was dissolved in an 80% (v/v) aqueous acetic acid for 20% (w/w) concentration and then added to the Chitosan/PEO blend solution (polymer solution) to obtain a polymer/extract solution with a polymer to extract weight ratio of 100/0 to 50/50. The polymer/extract solution were placed into a 5 mL plastic syringe and put into an electro spinner device. The electro spinning was done on the polyamide layer which was formed on collector at a previous step (example 3). The applied voltage, a nozzle to collector distance and an injection rate were fixed at 20 kV, 12 cm and 1 ml/h, respectively.

Example 5

Producing Chitosan Based Inner Layer

Chitosan/PEO solution was prepared as described in example 4. The Chitosan/PEO solution were placed into a 5 mL plastic syringe and put into an electro spinner device. The Electro spinning was done on a previous chitosan based middle layer. The applied voltage, a nozzle to collector distance and an injection rate were the same as in example 4.

Example 6

Cross-Linking Electro Spun Chitosan Based Nanofibers in Middle Layer by Genipin Genipin was first dissolved in ethanol with 10% (w/v) concentration. Genipin solution was then added to the polymer/extract solution (prepared similar to example 4) so that genipin was within 0.5 to 10 wt % of chitosan in the polymer/extract solution. This genipin including the polymer/extract solution was immediately electro spun on a polyamide layer in the same way as described in example 4. The resultant nanofibers of the middle layer so includes polymer, extract, and genipin. The inner layer then formed on this genipin includes polymer/extract fibrous layer. After a formation of the inner layer, the whole three layer mate was exposed to a water vapor at 30° C. for 24 h to complete a genipin-chitosan reaction in the middle layer and to obtain ultimate cross-linked nanofibers.

The wound dressing adheres to the wound surface and can be easily removed from the wound without any wound damage or pain. The wound contacting inner layer is made from the electro spun chitosan based nanofibers without any cross-linking. This non-cross-linked chitosan based inner layer acts as a gel forming layer in the presence of water which causes the dressing to be removed from the wound easily. On the other hand, the non-cross-linked chitosan inner layer can provide an antibacterial environment on the wound surface and accelerates a wound healing because of the antibacterial and wound healing acceleration properties of chitosan.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:

1. An electro spun nanofibrous wound dressing comprises:
    a first nanofibrous layer, and wherein the first nanofibrous layer is a polymeric layer, and wherein the first nanofibrous layer is an outer supporting layer, and wherein the first nanofibrous layer is hydrophobic in nature;
    a second nanofibrous layer, and wherein the second nanofibrous layer is a polymeric layer, and wherein the second nanofibrous layer is a genipin cross linked middle reservoir layer loaded with a herbal extract, wherein the genipin is present in the second nanofibrous layer at a ratio of 0.5-10% of chitosan by weight, and wherein a cross-linking of the chitosan based nanofibers with genipin decreases an initial burst release of a herbal extract and prolongs a release rate of the herbal extract, and wherein the second nanofibrous layer is hydrophobic or hydrophilic in nature, and wherein the herbal extract is a *melilotus officinalis* extract and wherein the cross-linking of the second nanofibrous layer controls a release of the *melilotus officinalis* extract in an aqueous environment;
    a third nanofibrous layer, and wherein the third nanofibrous layer is a polymeric layer, and wherein the third nanofibrous layer is a wound contacting inner layer, and wherein the third nanofibrous layer is a non-cross-linked chitosan based nanofibrous layer, and wherein the third nanofibrous layer is hydrophilic in nature; and additives, wherein the additives are selected from a group consisting of surfactants, block-co-polymers, salts and rubbers, and wherein the additives enhances a mechanical property and a chemical property of the wound dressing and wherein the additives controls a release profile of the herbal extract.

2. The wound dressing according to claim 1, wherein the first nanofibrous layer comprises a biocompatible polymers, and wherein the biocompatible polymers are a hydrophobic polymers, and wherein the hydrophobic polymers are selected from a group consisting of polyamides, polycaprolactone (PCL), poly(lactic acid) (PLA), poly(lactic-co-glycolic acid) (PLGA) and a combination thereof.

3. The wound dressing according to claim 1, wherein the first nanofibrous layer controls a vapour transmission rate and provides a moist environment on a surface of a wound to accelerate a wound healing process and wherein the first nanofibrous layer provides a barrier against a bacteria penetration thereby preventing the wound from an infection.

4. The wound dressing according to claim 1, wherein the second nanofibrous layer comprises a hydrophilic polymers or a hydrophobic polymers or a combination thereof and an extract of *Melilotus Officinalis*, and wherein the hydrophobic polymers are selected from a group consisting of polyamides, polycaprolactone (PCL), poly (lactic acid) (PLA), poly(lactic-co-glycolic acid) (PLGA), and a combination thereof, and wherein the hydrophilic polymers are selected from a group consisting of chitosan, gelatin, collagen, poly vinyl alcohol (PVA), polyethylene oxide (PEO), and a combination thereof, and wherein the hydrophilic polymer is chitosan.

5. The wound dressing according to claim 4, wherein the chitosan is present in the second nanofibrous layer at a ratio up to 90 weight percent of second nanofibrous layer or less.

6. The wound dressing according to claim 1, wherein the second nanofibrous layer comprises chitosan and poly ethylene oxide (PEO).

7. The wound dressing according to claim 1, wherein the extract of *melilotus officinalis* is mixed to the second nanofibrous layer at a ratio of 50%, or 30% or 10% of a total weight of the second nanofibrous layer.

8. The wound dressing according to claim 1, wherein the second nanofibrous layer has a high water absorption capability and wherein the second nanofibrous layer absorbs excess exudates coming out from a wound and wherein the second nanofibrous layer treats wounds with high exudates, and wherein the second nanofibrous layer is structurally stable in water.

9. The wound dressing according to claim 1, wherein the third nanofibrous layer comprises a biocompatible hydrophilic polymers and wherein the biocompatible hydrophilic polymers are selected from a group consisting of chitosan, collagen, gelatin, poly vinyl alcohol (PVA), polyethylene oxide (PEO) and a combination thereof.

10. The wound dressing according to claim 1, wherein the third nanofibrous layer comprises chitosan and poly ethylene oxide (PEO), and wherein chitosan is present in the third nanofibrous layer at a ratio of 90 weight percent of polymer or less.

11. The wound dressing according to claim 1, wherein the third nanofibrous layer forms a gel in presence of a water, and wherein a gel forming ability of the third nanofibrous layer helps the wound dressing to be removed from a wound easily in presence of a water, and wherein the third nanofibrous layer forms a barrier, and wherein the barrier controls a release of *Melilotus officinalis* extract from the second nanofibrous layer.

12. The wound dressing according to claim 1, wherein a release rate of the herbal extract depends on a type of polymer used, an amount of the herbal extract loaded, an extent of cross linking of the polymer and an addition of another polymer and additives.

13. A method of synthesizing an electro spun nanofibrous wound dressing comprises steps of:
   forming a first nanofibrous layer, wherein the first nanofibrous layer is a polymeric layer, and wherein the first nanofibrous layer is in a form of a mat, and wherein the first nanofibrous layer acts as a support layer for a second nanofibrous layer and a third nanofibrous layer;
   forming a second nanofibrous layer on the formed first nanofibrous layer, wherein the second nanofibrous layer is a polymeric layer, wherein the second nanofibrous layer is a chitosan polymer based nanofibrous layer loaded with *Melilotus officinalis* extract;
   forming a third nanofibrous layer on the formed second nanofibrous layer, wherein the third nanofibrous layer is a polymeric layer, wherein the third nanofibrous layer is a chitosan polymer based layer without *Melilotus officinalis* extract; and
   exposing the formed first nanofibrous layer, the second nanofibrous layer and the third nanofibrous layer to a water vapour at 30° C. for 24 h.

14. The method according to claim 13, wherein an electro spun nanofibrous wound dressing is synthesized by an electro spinning process and wherein the electro spinning process is carried out using an electro spinning device, wherein the electro spinning device is operated in a voltage range of 1-35 kV and a syringe pump wherein the syringe pump is controlled to provide a flow rate within a range of 0.1-100 ml/h.

15. The method according to claim 14, wherein the electro spinning process is carried out at a temperature of 30° C.

16. The method according to claim 14, wherein the electro spinning process is carried at a speed of 15 rpm.

17. The method according to claim 13, wherein the step of forming the first nanofibrous layer further comprises electro spinning a solution of polyamide 6,6, and wherein the solution of polyamide 6,6 is 20% (w/v) solution in a solvent, and wherein the solvent comprises a solution of formic acid and water in a ratio of 90/10 v/v, and wherein an electro spinning process is carried out at a voltage of 15 kV, and wherein a nozzle to a collector distance in an electro spinning device is kept at 10 cm and wherein an injection rate of the solution of polyamide 6,6 is fixed at 1 ml/h.

18. The method according to claim 13, wherein the step of forming the second nanofibrous layer further comprises:
   preparing a chitosan solution in 80% (v/v) aqueous acetic acid solution, and wherein the chitosan solution is a 3% by weight solution;
   preparing a poly ethylene oxide (PEO) solution in a 80% (v/v) aqueous acetic acid solution, and wherein the PEO solution is a 3% by weight solution;
   mixing the prepared chitosan solution and the prepared poly ethylene oxide (PEO) solution to form a blend solution of Chitosan and PEO in different weight ratios, wherein the different weight ratios are within 90/10 to 50/50;
   preparing a *melilotus officinalis* extract solution in a 80% (v/v) aqueous acetic acid, and wherein the *melilotus officinalis* extract solution has a concentration of 20% (w/w) concentration;
   mixing the prepared *melilotus officinalis* extract solution with the blend solution of Chitosan and PEO to obtain a polymeric extract solution with polymer to be extracted having a weight ratios of 100/0 to 50/50;

preparing a 10% genipin solution in ethanol;
adding the prepared genipin solution to the obtained polymeric extract solution, wherein the genipin is added at a ratio of 0.5 to 10 wt % of the chitosan in the polymeric extract solution;
electro spinning the polymeric extract solution including the genipin on the formed first nanofibrous layer, and wherein the electro spinning is done at a voltage of 20 kV, and wherein a distance between a nozzle to a collector of a electro spinning device is 12 cm and wherein an injection rate of the polymeric extract solution including the genipin is 1 ml/h.

19. The method according to claim 13, wherein the step of forming the third nanofibrous layer further comprises:
preparing a chitosan solution in 80% (v/v) aqueous acetic acid solution, and wherein the chitosan solution is a 3% by weight solution;
preparing a poly ethylene oxide (PEO) solution in a 80% (v/v) aqueous acetic acid solution, and wherein the PEO solution is a 3% by weight solution;
mixing the prepared chitosan solution and prepared poly ethylene oxide (PEO) solution to form a blend solution of Chitosan and PEO in different weight ratios, wherein the different weight ratios are within 90/10 to 50/50;
electro spinning the blend solution of Chitosan and PEO on the formed second nanofibrous layer, and wherein the electro spinning is done at a voltage of 20 kV, and wherein a distance between a nozzle to a collector of an electro spinning device is 12 cm and wherein an injection rate of the blend solution of Chitosan and PEO is 1 ml/h.

* * * * *